US008598539B2

(12) United States Patent
Chuang

(10) Patent No.: US 8,598,539 B2
(45) Date of Patent: Dec. 3, 2013

(54) GERMICIDAL DEVICE FOR ELEVATOR BUTTONS

(76) Inventor: Tsung-Tse Chuang, Taipei (TW)

( * ) Notice: Subject to any disclaimer, the term of this patent is extended or adjusted under 35 U.S.C. 154(b) by 16 days.

(21) Appl. No.: 13/365,364

(22) Filed: Feb. 3, 2012

(65) Prior Publication Data

US 2013/0200279 A1 Aug. 8, 2013

(51) Int. Cl.
*A61L 2/10* (2006.01)

(52) U.S. Cl.
USPC ................ 250/455.11; 250/492.1; 250/504 R

(58) Field of Classification Search
USPC ..................................................... 250/455.11
See application file for complete search history.

(56) References Cited

U.S. PATENT DOCUMENTS 5,861,633 A * 1/1999 Mandellos ................ 250/504 R
2011/0291995 A1* 12/2011 Shr et al. ........................ 345/176
2012/0240968 A1* 9/2012 Schumacher ................ 134/198

* cited by examiner

*Primary Examiner* — Phillip A Johnston
(74) *Attorney, Agent, or Firm* — WPAT, PC; Justin King

(57) ABSTRACT

A germicidal device for elevator buttons includes a casing and a lamp tube installed inside the casing and capable of emitting germicidal light. The casing can be fixedly mounted on an elevator control panel for the germicidal light emitted from the lamp tube to project onto all elevator buttons on the elevator control panel, so as to continuously kill any germs on the elevator buttons. The casing is provided on a bottom with an elongated slot, via which the germicidal light emitted from the lamp tube is outward projected onto all the elevator buttons. The lamp tube can be a UV germicidal lamp tube for emitting UV germicidal light.

8 Claims, 5 Drawing Sheets

GERMICIDAL DEVICE FOR ELEVATOR BUTTONS

FIELD OF THE INVENTION

The present invention relates to a germicidal device for elevator buttons, and more particularly, to a germicidal device capable of continuously kill germs on elevator buttons in a convenient manner while providing good germicidal effect.

BACKGROUND OF THE INVENTION

It is reported that there is a large number of germs on the computer keyboard. Since the germs on the computer keyboard generally come from the same user or the user's families, they do not really form a big threat to the users. On the other hand, there is also a large number of germs on the elevator buttons in many public places and these germs come from different people and are various in types, including bacteria that transmit infectious diseases. To avoid being infected with such germs or bacteria, hand sanitizer spray or dry hand sanitizer is frequently provided in elevator halls for people to use before and after pressing the elevator buttons, so as to clean and disinfect their hands. Particularly, such hand sanitizer spray or dry hand sanitizer has become prerequisite in hospitals or medical care related places.

However, most people are lazy and would rather take risks than clean their hands with the hand sanitizer spray or dry hand sanitizer. Such passive type of disinfection often loses it function due to people's laziness and negligence. Therefore, only an active germicidal means that does not require people to operate can help people to get the highest and exactest hygienic safety in the public places.

In view that the elevator buttons are used by people everyday while there is not a proper germicidal device particularly provided for the elevator buttons, it is therefore tried by the inventor to develop a germicidal device for elevator buttons that is able to continuously disinfect the elevator buttons to increase the hygienic safety in using elevators.

SUMMARY OF THE INVENTION

A primary object of the present invention is to provide a germicidal device for elevator buttons, which is mounted on an elevator control panel for continuously disinfecting elevator buttons provided on the elevator control panel, so as to stop germs from propagating via elevator buttons.

To achieve the above and other objects, the germicidal device for elevator buttons according to the present invention includes a casing and a lamp tube installed inside the casing for emitting germicidal light. The casing is fixed on the elevator control panel and is provided on a bottom with an elongated slot, via which the germicidal light emitted from the lamp tube is outward projected onto an area of the elevator control panel covering all the elevator buttons to kill germs thereon.

The germicidal device can be mounted on the elevator control panel above the elevator buttons, so that the emitted germicidal light is downward projected onto the elevator buttons. Alternatively, the germicidal device can be mounted on the elevator control panel below the elevator buttons, so that the emitted germicidal light is upward projected onto the elevator buttons.

In the germicidal device according to the present invention, the lamp tube can be an ultraviolet (UV) germicidal lamp tube capable of emitting UV germicidal light.

In the germicidal device according to the present invention, the casing includes a main support, a left stopper, a right stopper, and a slidable cover. The main support is fixedly screwed to the elevator control panel above the elevator buttons and has a transversely extended open front as well as a left and a right open end. The left and the right stopper close the left and the right open end of the main support, respectively; and the lamp tube is installed inside the main support. The slidable cover is connected to the main support to close the open front and shield the lamp tube.

In the germicidal device according to the present invention, the main support is provided along an upper edge of the open front with an upward facing first guide channel, and along a lower edge of the open front with a downward facing second guide channel; and the slidable cover is provided on a rear side along an upper edge thereof with a downward bent first flange for correspondingly inserting into the first guide channel, and along a lower edge thereof with an upward bent second flange for correspondingly inserting into the second guide channel. Therefore, the slidable cover connected to the main support via engagement of the first and second flanges with the first and second guide channels, respectively, is laterally movable relative to the main support. The left and the right stopper respectively have a stop screw threaded into a front side thereof to press against a left and a right end of the slidable cover when the latter is connected to the main support.

In the germicidal device for elevator buttons according to the present invention, the casing is provided with a power switch for controlling power supply to the lamp tube.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENTS

The present invention will now be described with a preferred embodiment thereof and with reference to the accompanying drawings.

Figure 1:
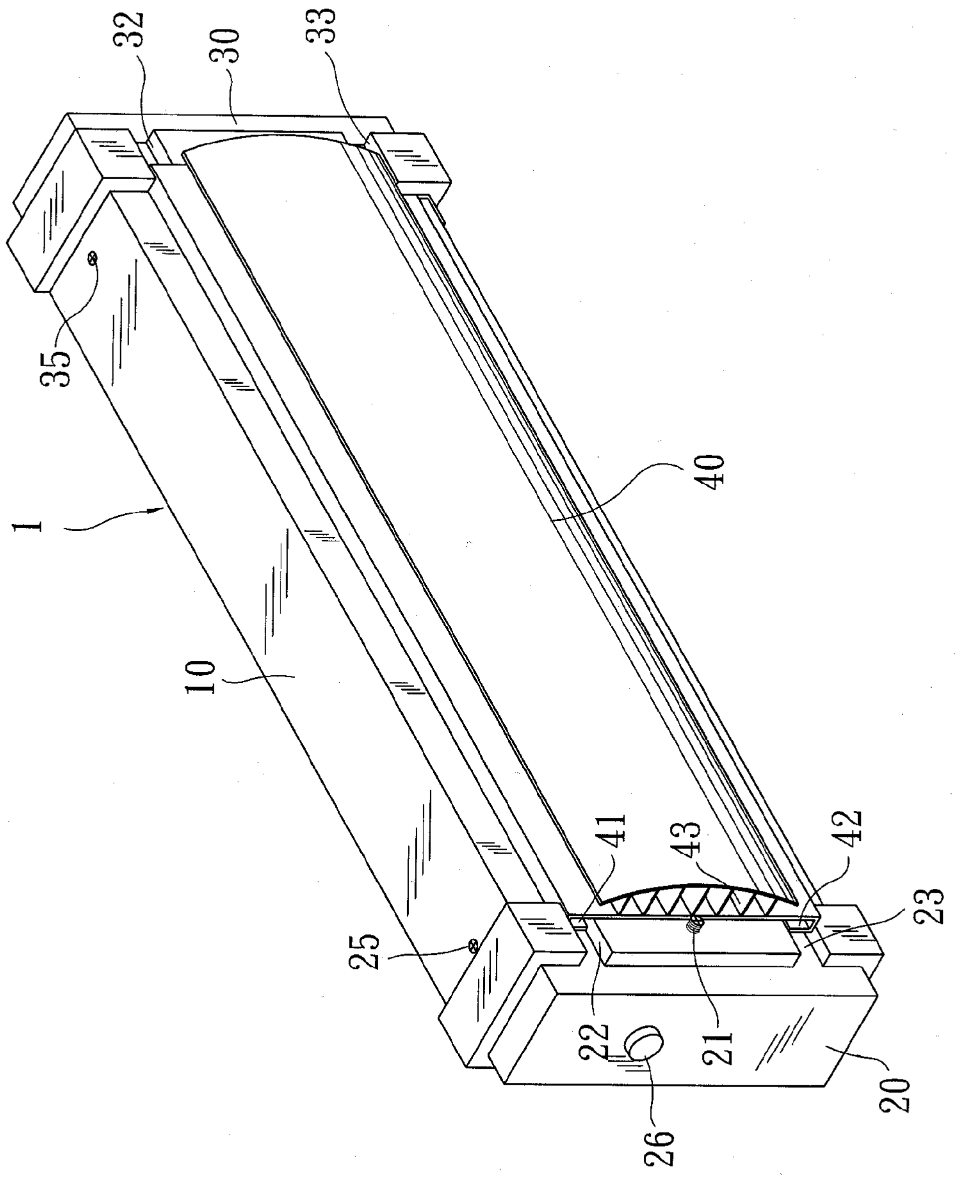
FIG. 1 is an assembled perspective view of a germicidal device for elevator buttons according to an embodiment of the present invention.
Figure 2:
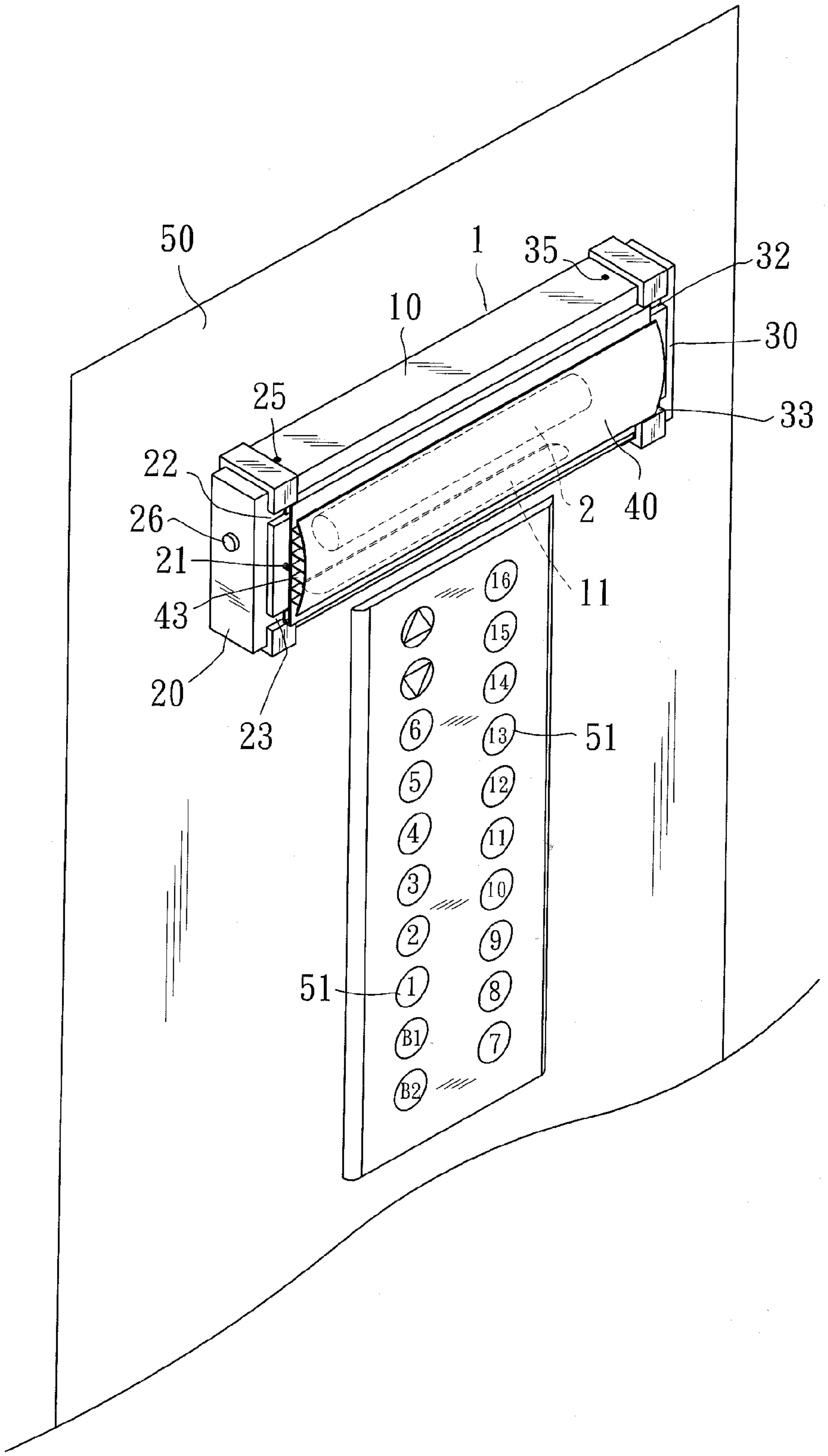
FIG. 2 is a front perspective view showing the germicidal device of FIG. 1 is mounted on an elevator control panel above elevator buttons for use.
Figure 3:
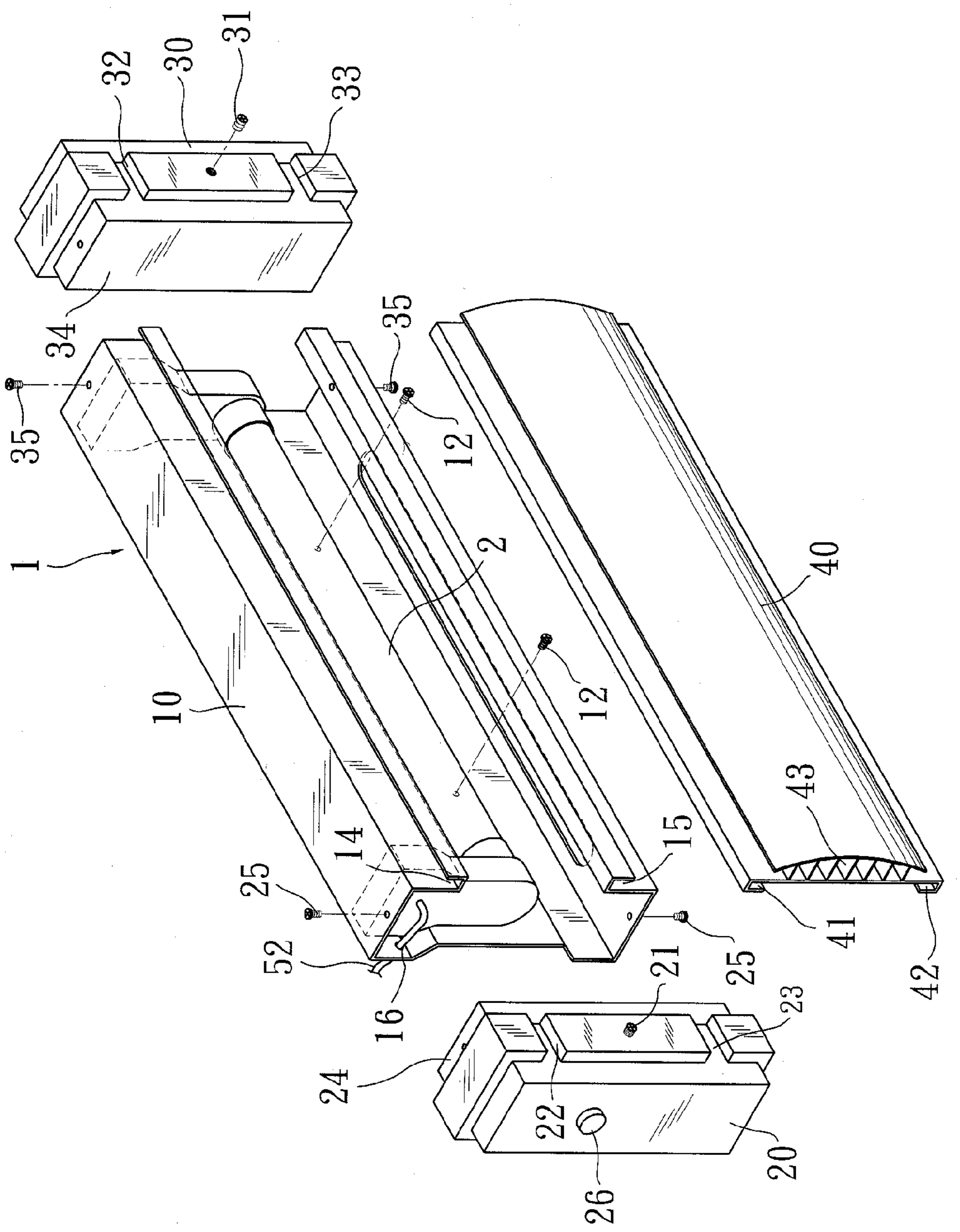
FIG. 3 is an exploded view of FIG. 1.

Please refer to FIGS. 1 to 3. The germicidal device for elevator buttons according to an embodiment of the present invention is mounted on an elevator control panel 50 to continuously emit germicidal light, such as ultraviolet (UV) light, toward a plurality of elevator buttons 51, which are provided on the elevator control panel 50 for users to press and choose a floor or the like, so that the elevator buttons 51 are UV sterilized. As shown, the germicidal device of the present invention includes a casing 1 and a lamp tube 2 installed in the casing 1 for producing germicidal light. The lamp tube 2 can be a UV germicidal lamp tube 2 capable of emitting UV germicidal light. The casing 1 can be fixedly mounted on the elevator control panel 50 above the elevator buttons 51, and is provided on a bottom with an elongated slot 11, via which the UV germicidal light emitted from the UV germicidal lamp tube 2 is outward projected onto an area covering all the elevator buttons 51, so that all the elevator buttons 51 are subjected to UV sterilization.

Figure 4:
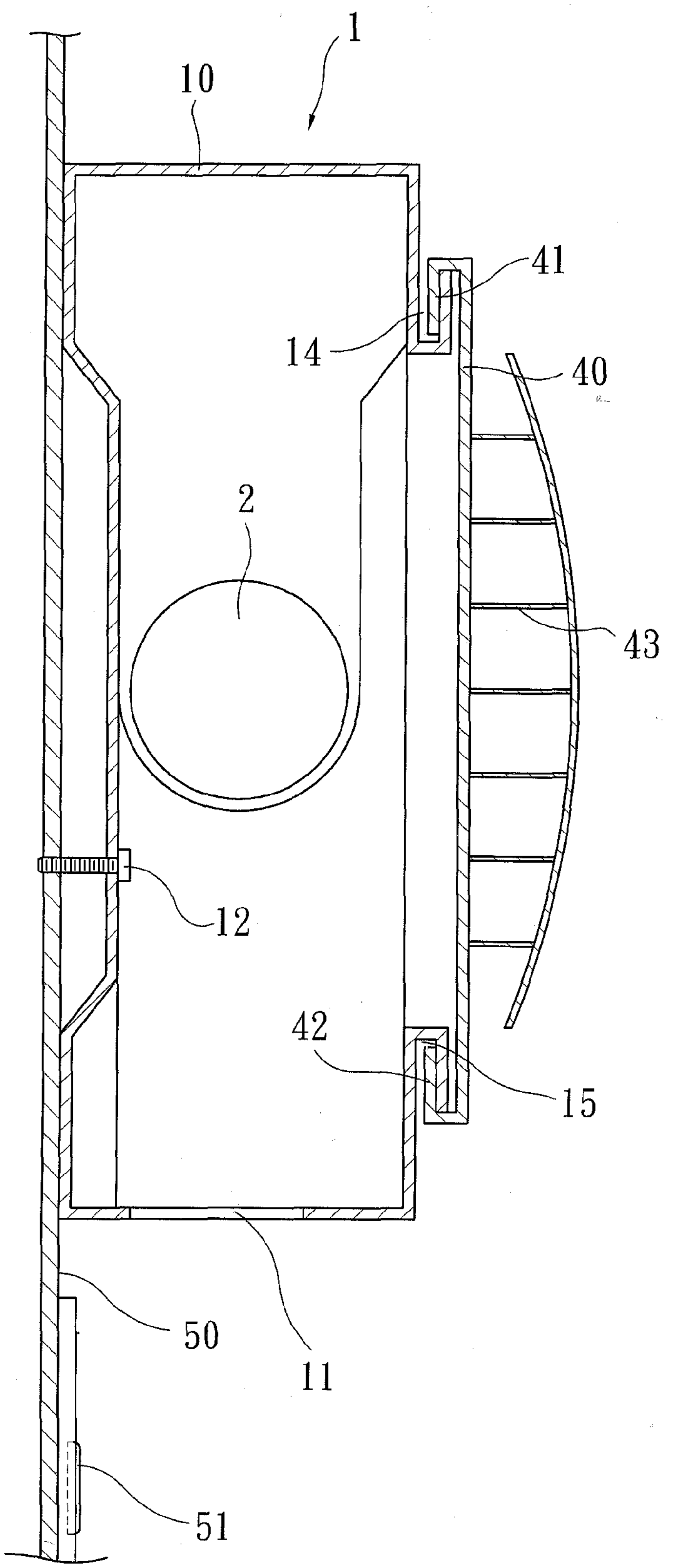
FIG. 4 is a sectional side view of FIG. 2 showing a first manner of mounting the germicidal device on the elevator control panel.
Figure 5:
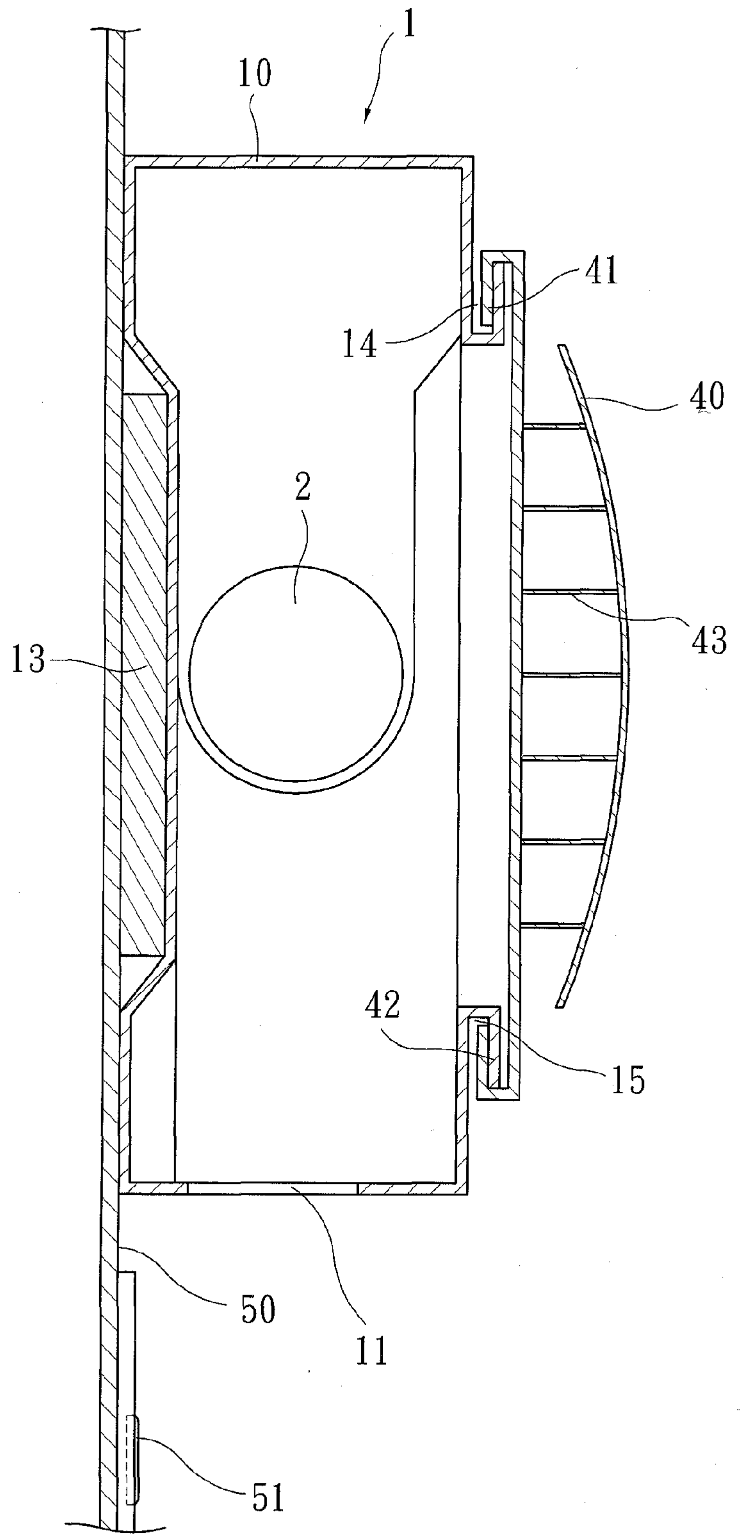
FIG. 5 is a sectional side view of FIG. 2 showing a second manner of mounting the germicidal device on the elevator control panel.

The casing 1 includes a main support 10, a left stopper 20, a right stopper 30, and a slidable cover 40. The main support 10 is fixed to the elevator control panel 50 and has a substantially U-shaped cross section to include an open front as well as a left and a right open end. The lamp tube 2 is installed in the main support 10. The main support 10 may be fixed to the elevator control panel 50 with screws 12 as shown in FIG. 4, or with double-side adhesive tapes 13 providing sufficient adhesion force as shown in FIG. 5. The elongated slot 11 is provided on the bottom of the main support 10 to serve as an opening for the germicidal light to pass therethrough. The main support 10 can be fixed to the elevator control panel 50 above the elevator buttons 51, so that the germicidal light emitted from the lamp tube 2 and passing through the elongated slot 11 is downward irradiated onto all the buttons 51. The left stopper 20 and the right stopper 30 close the left and the right open end of the main support 10, respectively. The slidable cover 40 is connected to the main support 10 to close the open front of the main support 10 and shield the lamp tube 2.

The left stopper 20 is provided on a right side with a plug portion 24 adapted to be fitly plugged into the left open end of the main support 10. Screws 25 are threaded through the main support 10 into upper and lower ends of the plug portion 24, so as to fixedly connect the left stopper 20 to the main support 10. Similarly, the right stopper 30 is provided on a left side with a plug portion 34 adapted to be fitly plugged into the right open end of the main support 10, and screws 35 can be threaded through the main support 10 into upper and lower ends of the plug portion 34 to fixedly connect the right stopper 30 to the main support 10.

The main support 10 is provided along an upper edge of the open front with an upward facing first guide channel 14, and along a lower edge of the open front with a downward facing second guide channel 15. The slidable cover 40 is provided on a rear side along an upper edge thereof with a downward bent first flange 41 for correspondingly inserting into the first guide channel 14, and along a lower edge thereof with an upward bent second flange 42 for correspondingly inserting into the second guide channel 15. By laterally guiding the first and the second flange 41, 42 into the first and the second guide channel 14, 15, respectively, the slidable cover 40 is laterally movably installed on the main support. Then, two stop screws 21, 31 are screwed into front side of the left stopper 20 and of the right stopper 30, respectively, to press against left and right ends of the slidable cover 40, so that the slidable cover 40 is held to the position of closing the open front of the main support 10 without moving laterally relative to the main support 10. Further, the left and the right stopper 20, 30 are provided on respective front side with upper and lower grooves 22, 23 and 32, 33 for the first and the second flange 41, 42 of the slidable cover 40 to move therein, such that the left and the right stopper 20, 30 do not stop the slidable cover 40 from sliding relative to the main support 10 when the stop screws 21, 31 are removed.

The slidable cover 40 can be made of aluminum through extrusion and includes a plurality of radiating fins 43 to provide heat dissipation function. In practical operation of the present invention, the slidable cover 40 has a temperature ranged from about 25° C. to about 30° C. that would not cause any uncomfortable feeling to a person who touches the slidable cover 40. Since heat produced by the lamp tube 2 during operation thereof can be continuously dissipated into ambient air via the slidable cover 40, an interior of the main support 10 can always be maintained in a low temperature state.

The main support 10 is provided at a predetermined position with a through hole 16, via which a power cord 52 inside an elevator car can be guided into the main support 10 to serve as a power cord of the UV germicidal lamp tube 2. A power switch 26 can be further provided on the casing 1 for controlling power supply to the UV germicidal lamp tube 2. In the present invention, the power switch 26 can be provided on the left stopper 20 or the right stopper 30, so that the power supply to the lamp tube 2 can be controlled from outside of the casing 1. In practical application of the present invention, the power switch 26 may also be arranged inside the casing 1. For example, for the elevator button germicidal device used in a hospital, the power switch 26 may be arranged inside the casing 1, lest the power supply should be inadvertently cut off by some elevator passenger.

The elongated slot 11 provided on the bottom of the casing 1 is preferably arranged at a position close to the elevator control panel 50. The elongated slot 11 has a length larger than a width covered by all vertical rows of the elevator buttons 41 on the elevator control panel 50, so that the UV germicidal light emitted from the lamp tube 2 can be exactly irradiated on all the elevator buttons 51. The position and the width of elongated slot 11 must be so designed that a small child raising his or her head would not directly see the UV germicidal lamp tube 2 via the elongated slot 11.

In the illustrated embodiment, the germicidal device is mounted above the elevator buttons 51. The germicidal light emitted from the UV germicidal lamp tube 2 installed inside the casing 1 is projected downward onto the elevator buttons 51. In practical application of the present invention, the germicidal device can be otherwise installed below or to one lateral side of the elevator buttons 51 with the elongated slot 11 always facing toward the elevator buttons 51. The lamp tube 2 may also be an ozone UV germicidal lamp tube 2 capable of producing ozone in air to provide further upgraded germicidal function.

After being switched on, the germicidal device of the present invention is able to continuously kill germs on the elevator buttons 51, allowing elevator passengers to safely press the buttons without the risk of getting contact with any germs. The germicidal device of the present invention can be used in place of the hand sanitizer spray generally provided in an elevator hall near elevator doors. Therefore, small baskets hung on the wall for holding hand sanitizer spray can be omitted to give the elevator hall an integral and beautiful appearance.

The present invention has been described with a preferred embodiment thereof and it is understood that many changes and modifications in the described embodiment can be carried out without departing from the scope and the spirit of the invention that is intended to be limited only by the appended claims.

What is claimed is:

1. A germicidal device for providing a germicidal effect to a plurality of elevator buttons, comprising:

a casing disposed above said plurality of elevator buttons comprising:

a main support, comprising:

an open front, transversely extended;

a left open end;

a right open end; and an elongated slot, disposed on a bottom side of said main support;

a left stopper, disposed on said left open end;

a right stopper, disposed on said right open end;

a lamp tube, disposed within said main support and emitting germicidal light; and a slidable cover, disposed on said open front and shielding said lamp tube;

wherein said casing is disposed upon an elevator control panel, and germicidal light emitted from said lamp tube is outward projected through said elongated slot onto said plurality of elevator buttons to kill germs thereon.

2. The germicidal device for providing a germicidal effect to a plurality of elevator buttons as claimed in claim 1, said main support further comprises:

an upward facing first guide channel, disposed on an upper edge of said open front; and a downward facing second guide channel, disposed on a lower edge of said open front;

wherein said slidable cover further comprises a downward bent first flange for correspondingly inserting into said first guide channel; and an upward bent second flange for correspondingly inserting into said second guide channel; whereby said slidable cover is disposed on said main support via engagement of the first and second flanges with the first and second guide channels, respectively, and said slidable cover is laterally movable relative to the main support.

3. The germicidal device for providing a germicidal effect to a plurality of elevator buttons as claimed in claim 1, wherein the left stopper and the right stopper each have a stop screw threaded into a front side thereof for pressing against a left and a right end of the slidable cover, respectively, when the latter is connected to the main support.

4. The germicidal device for providing a germicidal effect to a plurality of elevator buttons as claimed in claim 1, wherein the main support is provided at a predetermined position with a through hole, via which a power cord inside an elevator car can be guided into the main support to serve as a power cord of the lamp tube.

5. The germicidal device for providing a germicidal effect to a plurality of elevator buttons as claimed in claim 1, wherein the slidable cover is made of an aluminum material through extrusion, and includes a plurality of radiating fins to provide heat dissipation function.

6. The germicidal device for providing a germicidal effect to a plurality of elevator buttons as claimed in claim 1, wherein the casing is fixedly mounted above the elevator buttons, such that the germicidal light emitted from the lamp tube is downward projected onto all the elevator buttons.

7. The germicidal device for providing a germicidal effect to a plurality of elevator buttons as claimed in claim 1, wherein the casing is provided with a power switch for controlling power supply to the lamp tube.

8. The germicidal device for providing a germicidal effect to a plurality of elevator buttons as claimed in claim 1, wherein the lamp tube is an ultraviolet (UV) germicidal lamp tube capable of emitting UV germicidal light.

* * * * *